United States Patent
Parthasaradhi et al.

(10) Patent No.: US 7,560,560 B2
(45) Date of Patent: Jul. 14, 2009

(54) CRYSTALLINE FORMS OF DONEPEZIL HYDROCHLORIDE

(75) Inventors: Reddy Bandi Parthasaradhi, Hyderabad (IN); Reddy Kura Rathnakar, Hyderabad (IN); Reddy Rapolu Raji, Hyderabad (IN); Reddy Dasari Muralidhara, Hyderabad (IN); Reddy Kesireddy Subash Chander, Hyderabad (IN)

(73) Assignee: Hetero Drugs Limited, Hyderabad, IN (US)

( * ) Notice: Subject to any disclaimer, the term of this patent is extended or adjusted under 35 U.S.C. 154(b) by 446 days.

(21) Appl. No.: 10/511,735

(22) PCT Filed: Apr. 16, 2003

(86) PCT No.: PCT/IN03/00158

§ 371 (c)(1), (2), (4) Date: Oct. 18, 2004

(87) PCT Pub. No.: WO2004/092137

PCT Pub. Date: Oct. 28, 2004

(65) Prior Publication Data

US 2005/0215591 A1 Sep. 29, 2005

(51) Int. Cl.
C07D 211/06 (2006.01)

(52) U.S. Cl. .................. 546/206; 546/205; 514/319
(58) Field of Classification Search ............ 546/205, 546/206; 514/319
See application file for complete search history.

(56) References Cited

U.S. PATENT DOCUMENTS

| 6,140,321 | A | 10/2000 | Imai et al. |
| 2004/0102523 | A1 | 5/2004 | Broquaire et al. |

FOREIGN PATENT DOCUMENTS

| EP | 296560 | | 12/1988 |
| EP | 1211243 | * | 6/2002 |
| EP | 1323712 | | 7/2003 |
| WO | 97/46527 | * | 12/1997 |
| WO | 2007/015052 | * | 2/2007 |

OTHER PUBLICATIONS

Kirk-Othmer encyclopedia of chemical technology "crystallization" p. 1-7, Aug. 16, (2002).*
Merck Index "chloroform" (2006).*
PCT International Search Report dated Apr. 16, 2003.

* cited by examiner

*Primary Examiner*—Celia Chang
(74) *Attorney, Agent, or Firm*—Caesar, Rivise, Bernstein, Cohen & Pokotilow, Ltd.

(57) ABSTRACT

The present invention provides novel crystalline forms of donepezil hydrochloride, processes for their preparation and pharmaceutical compositions containing them.

6 Claims, 4 Drawing Sheets

CRYSTALLINE FORMS OF DONEPEZIL HYDROCHLORIDE

FIELD OF THE INVENTION

The present invention provides novel crystalline forms of donepezil hydrochloride, processes for their preparation and pharmaceutical compositions containing them.

BACKGROUND OF THE INVENTION

Donepezil hydrochloride of formula (1):

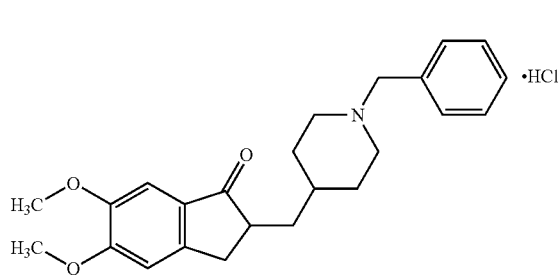

or 2,3-Dihydro-5,6-dimethoxy-2-[[1-(phenylmethyl)-4-piperidinyl]methyl]-1H-inden-1-one hydrochloride is useful for prevention and treatment of alzheimer disease. The therapeutic uses of donepezil hydrochloride and related compounds are disclosed in EP 296560.

U.S. Pat. No. 6,140,321 disclosed four crystalline forms of donepezil hydrochloride, polymorph (I), polymorph (II), polymorph (III) and polymorph (IV) and processes for preparation thereof.

It has now been discovered that donepezil hydrochloride can be prepared in four stable crystalline forms having good dissolution characteristics.

The object of the present invention is to provide stable novel crystalline forms of donepezil hydrochloride, processes for preparing these forms and pharmaceutical compositions containing them.

DETAILED DESCRIPTION OF THE INVENTION

In accordance with the present invention, there is provided a novel crystalline form of donepezil hydrochloride, designated as form H1, characterized by an x-ray powder diffraction spectrum having peaks expressed as 2θ at about 15.2, 18.7, 20.6, 22.3, 23.5, 24.0, 24.6, 27.0, 29.0 and 30.5 degrees. FIG. 1 shows typical form H1 x-ray powder diffraction spectrum.

In accordance with the present invention, a process is provided for preparation of donepezil hydrochloride form H1, which comprises:
a) dissolving donepezil free base in ethylene dichloride;
b) adding hydrochloric acid; and
c) precipitating donepezil hydrochloride form H1 from the solution formed in (b) by adding an anti-solvent.

Preferably, the quantity of hydrochloric acid is 0.5 to 2.0 mole per mole of donepezil. The anti-solvent should be added in the quantity that causes the precipitation of donepezil hydrochloride under the conditions of experiment. Preferable anti-solvents are diisopropyl ether, n-hexane, n-heptane and diethyl ether. A mixture of anti-solvents may also be used.

In accordance with the present invention, an another process is provided for preparation of donepezil hydrochloride form H1, which comprises:

a) dissolving donepezil free base in ethylene dichloride;
b) precipitating donepezil hydrochloride form H1 from the solution formed in (a) by adding an anti-solvent.

Donepezil hydrochloride in any form, crystalline, amorphous or solvated form, may be used in (a). The anti-solvent should be added in a quantity that causes the precipitation of donepezil hydrochloride under the conditions of experiment. Preferable anti-solvents are diisopropyl ether, n-hexane, n-heptane and diethyl ether. A mixture of anti-solvents may also be used.

In accordance with the present invention, there is provided a novel crystalline form of donepezil hydrochloride, designated as form H2, characterized by an x-ray powder diffraction spectrum having peaks expressed as 2θ at about 6.6, 6.8, 10.1, 12.8, 13.7, 15.0, 15.6, 16.5, 17.3, 18.4, 19.5, 19.8, 20.0, 21.6, 21.9, 22.3, 23.9, 24.2, 24.7, 25.3, 26.0, 26.9 and 28.2 degrees. FIG. 2 shows typical form H2 x-ray powder diffraction spectrum.

In accordance with the present invention, a process is provided for preparation of donepezil hydrochloride form H2, which comprises:
a) dissolving donepezil free base in toluene;
b) adding hydrochloric acid; and
c) isolating donepezil hydrochloride form H2 by filtration or centrifugation.

Preferably, the quantity of hydrochloric acid is 0.5 to 2.0 mole per mole of donepezil.

In accordance with the present invention, there is provided a novel crystalline form of donepezil hydrochloride monohydrate, characterized by an x-ray powder diffraction spectrum having peaks expressed as 2θ at about 5.0, 10.0, 12.7, 13.2, 16.2, 20.0, 21.3, 23.1, 23.9 and 25.3 degrees. FIG. 3 shows donepezil hydrochloride monohydrate x-ray powder diffraction spectrum.

In accordance with the present invention, a process is provided for preparation of donepezil hydrochloride monohydrate, which comprises:
a) dissolving donepezil free base in a mixture of chloroform and water;
b) adding hydrochloric acid; and
c) precipitating donepezil hydrochloride monohydrate from the solution formed in (b) by adding an anti-solvent.

The water can be added directly or in the form of, for example, as an aqueous solution of hydrochloric acid. Preferably, the quantity of hydrochloric acid is 0.5 to 2.0 mole per mole of donepezil. Preferable anti-solvents are diisopropyl ether, n-hexane, n-heptane and diethyl ether. A mixture of anti-solvents may also be used.

In accordance with the present invention, an another process is provided for preparation of donepezil hydrochloride monohydrate, which comprises:
a) dissolving donepezil hydrochloride in a mixture of chloroform and water; and
b) precipitating donepezil hydrochloride monohydrate from the solution formed in (a) by adding an anti-solvent.

Donepezil hydrochloride in any form, crystalline, amorphous or solvated form, may be used in (a). The anti-solvent should be added in a quantity that causes the precipitation of donepezil hydrochloride under the conditions of experiment. Preferable anti-solvents are diisopropyl ether, n-hexane, n-heptane and diethyl ether. A mixture of anti-solvents may also be used.

In accordance with the present invention, there is provided a novel crystalline form of donepezil hydrochloride sesquihydrate, characterized by an x-ray powder diffraction spectrum having peaks expressed as 2θ at about 5.1, 10.8, 12.8, 13.3, 13.9, 15.0, 16.3, 17.1, 17.7, 19.5, 20.1, 21.4, 23.2, 24.1, 26.6, 27.3, 28.2, 29.7, 31.9 and 35.3 degrees. FIG. 4 shows donepezil hydrochloride sesquihydrate x-ray powder diffraction spectrum.

In accordance with the present invention, a process is provided for preparation of donepezil hydrochloride sesquihydrate, which comprises:
a) dissolving donepezil free base in a mixture of tert-butyl alcohol and water;
b) adding hydrochloric acid; and
c) isolating donepezil hydrochloride sesquihydrate by filtration or centrifugation.

The water can be added directly or in the form of, for example, as an aqueous solution of hydrochloric acid. Preferably, the quantity of hydrochloric acid is 0.5 to 2.0 mole per mole of donepezil.

Donepezil free base and donepezil hydrochloride used in the above processes can be obtained from the previously known methods.

In accordance with the present invention, there is provided a pharmaceutical composition comprising donepezil hydrochloride form H1 and pharmaceutically acceptable carrier or diluent.

In accordance with the present invention, there is provided a pharmaceutical composition comprising donepezil hydrochloride form H2 and pharmaceutically acceptable carrier or diluent.

In accordance with the present invention, there is provided a pharmaceutical composition comprising donepezil hydrochloride monohydrate and pharmaceutically acceptable carrier or diluent.

In accordance with the present invention, there is provided a pharmaceutical composition comprising donepezil hydrochloride sesquihydrate and pharmaceutically acceptable carrier or diluent.

Figure 1:
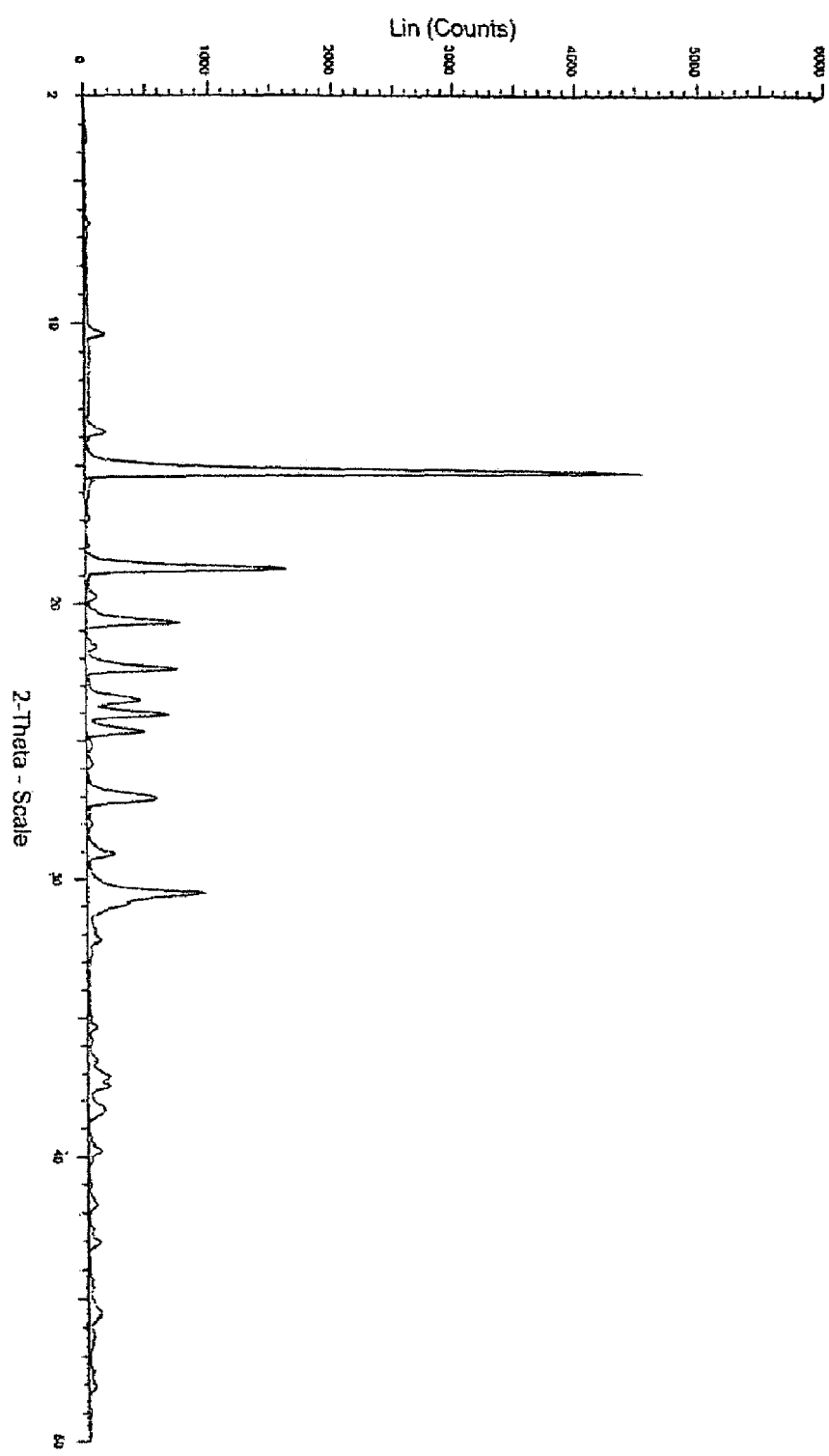
FIG. 1 is a x-ray powder diffraction spectrum of Donepezil hydrochloride form H1.
Figure 2:
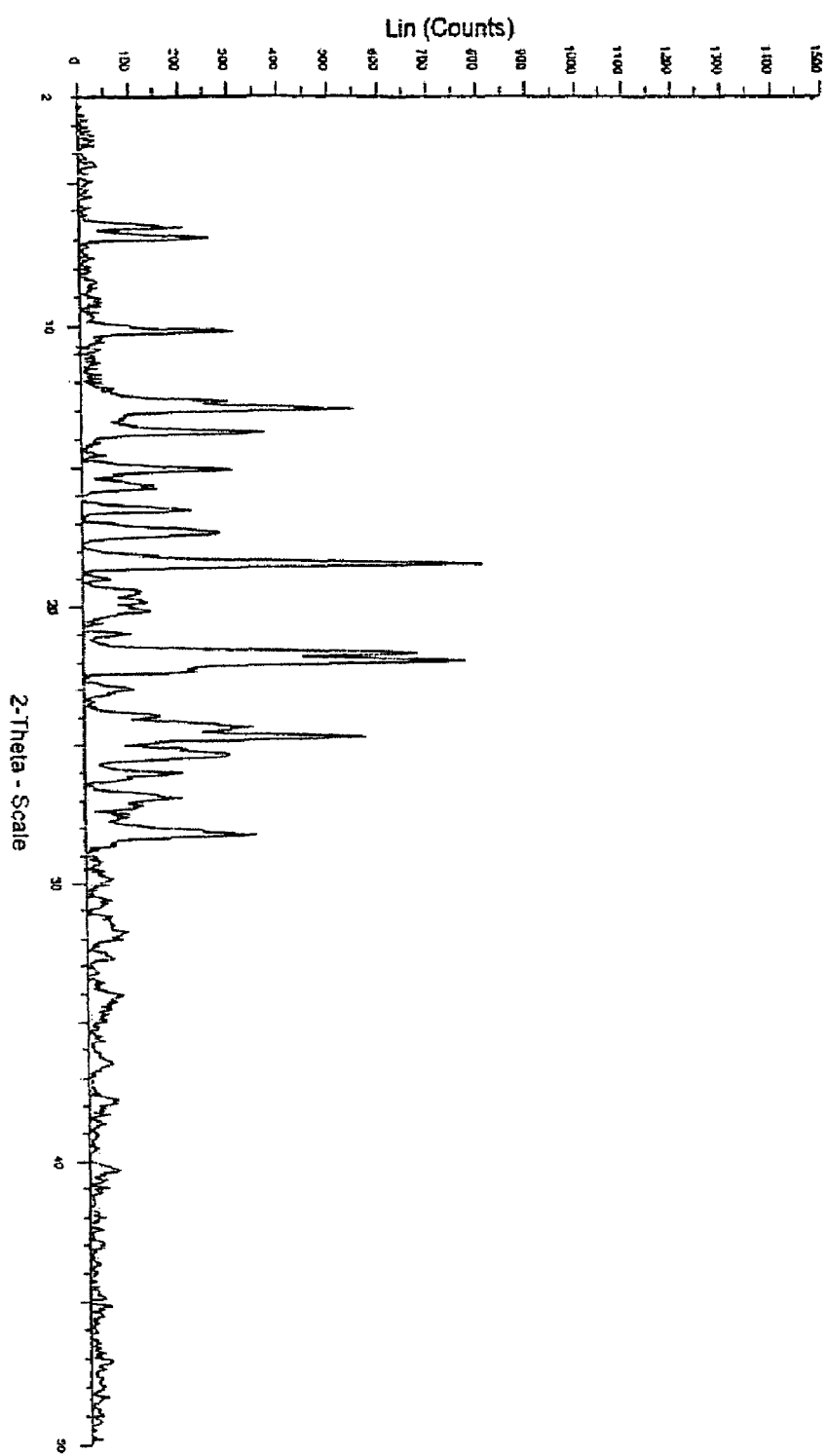
FIG. 2 is a x-ray powder diffraction spectrum of Donepezil hydrochloride form H2.
Figure 3:
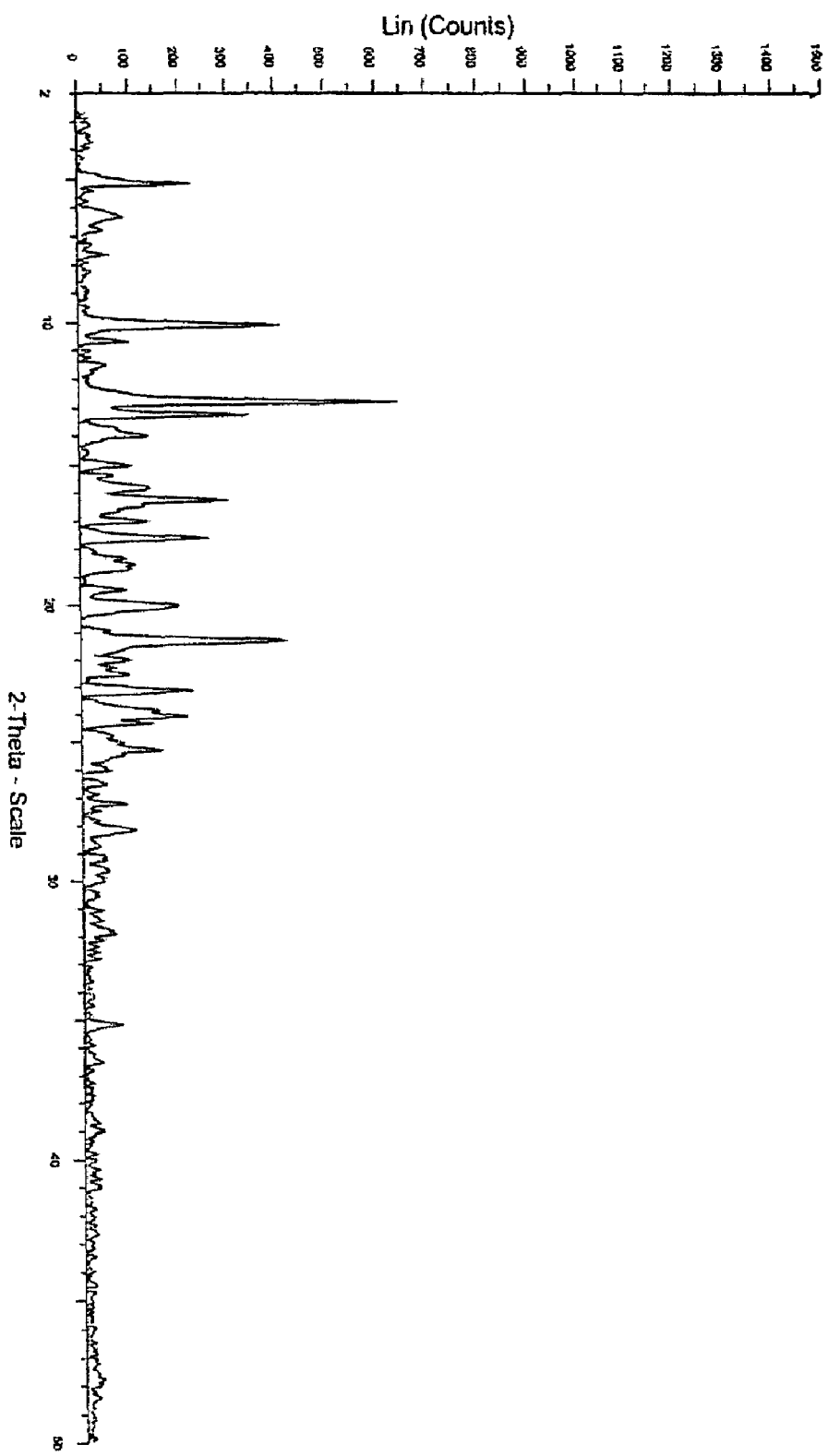
FIG. 3 is a x-ray powder diffraction spectrum of donepezil hydrochloride monohydrate.
Figure 4:
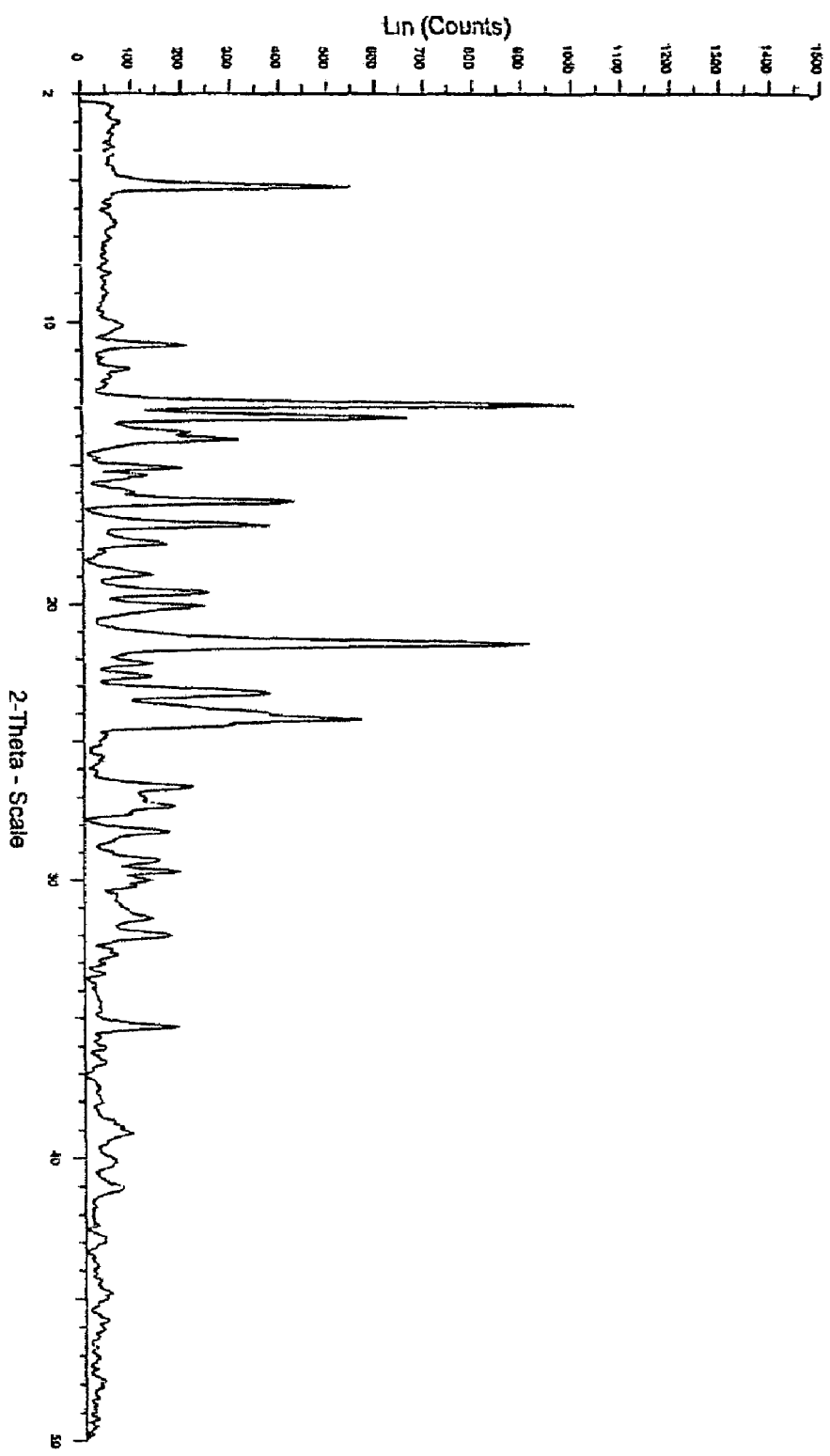
FIG. 4 is a x-ray powder diffraction spectrum of donepezil hydrochloride sesquihydrate.

x-Ray powder diffraction spectrum was measured on a Bruker axs D8 advance x-ray powder diffractometer having a copper-K$\alpha$ radiation.

The following examples further illustrate the present invention.

EXAMPLE 1

Donepezil free base (4.0 gm) is dissolved in ethylene dichloride (20 ml) at 27° C., conc. hydrochloric acid (1.2 ml) is added to the solution and stirred for 2 hours at 25° C. to 30° C. Then diisopropyl ether (75 ml) is added and the precipitated solid is filtered off and dried to give 3.0 gm of donepezil hydrochloride form H1.

EXAMPLE 2

Donepezil free base (10.0 gm) is dissolved in toluene (50 ml) at 25° C., conc. hydrochloric acid (2.8 ml) is added to the solution and stirred for 6 hours at 25° C. to 30° C. The crystals formed are filtered and dried to give 8.2 gm of donepezil hydrochloride form H2.

EXAMPLE 3

Donepezil hydrochloride form H2 (5.0 gm) is added to ethylene dichloride (100 ml), the contents are heated to 55° C. and stirred for 8 hours at 55° C. to 60° C. The solution so obtained is cooled to 25° C., diisopropyl ether (100 ml) is added to the solution and precipitated solid is filtered and dried to give 4.3 gm of donepezil hydrochloride form H1.

EXAMPLE 4

Donepezil free base (4.0 gm) is dissolved in a mixture of chloroform (20 ml) and water (1 ml) at 25° C., conc. hydrochloric acid (1.4 ml) is added to the solution and stirred for 3 hours at 25° C. to 30° C. Then diisopropyl ether (100 ml) is added and precipitated solid is filtered off and dried to give 4.0 gm of donepezil hydrochloride monohydrate.

EXAMPLE 5

Donepezil hydrochloride form H2 (5.0 gm) is added to a mixture of chloroform (100 ml) and water (1.5 ml), the contents are heated to 45° C. and stirred for 8 hours at 45° C. to 50° C. The solution so obtained is cooled to 25° C., diisopropyl ether (100 ml) is added to the solution and precipitated solid is filtered and dried to give 4.1 gm of donepezil hydrochloride monohydrate.

EXAMPLE 6

Donepezil free base (4.0 gm) is dissolved in a mixture of tert-butyl alcohol (30 ml) and water (1.5 ml) at 27° C., conc. hydrochloric acid (1.2 ml) is added to the solution and stirred for 3 hours at 25° C. to 30° C. The crystals so obtained are filtered and dried to give 3.5 gm of donepezil hydrochloride sesquihydrate.

We claim:

1. A process for the preparation of donepezil hydrochloride monohydrate characterized by an x-ray powder diffraction spectrum having peaks expressed as 2θ at about 5.0, 10.0, 12.7, 13.2, 16.2, 20.0, 21.3, 23.1, 23.9 and 25.3 degrees, which comprises the steps of: a) dissolving donepezil free base in a mixture of chloroform and water; b) adding hydrochloric acid; and c) precipitating donepezil hydrochloride monohydrate from the solution formed in (b) by adding an anti-solvent.

2. The process according to claim 1, wherein the anti-solvent is diisopropyl ether, n-hexane, n-heptane or diethyl ether.

3. The process according to claim 1, wherein the anti-solvent is diisopropyl ether.

4. A process for preparation of donepezil hydrochloride monohydrate characterized by an x-ray powder diffraction spectrum having peaks expressed as 2θ at about 5.0, 10.0, 12.7, 13.2, 16.2, 20.0, 21.3, 23.1, 23.9 and 25.3 degrees, which comprises the steps of: a) dissolving donepezil hydrochloride in a mixture of chloroform and water; and b) precipitating donepezil hydrochloride monohydrate from the solution formed in (a) by adding an anti-solvent.

5. The process according to claim 4, wherein the anti-solvent is diisopropyl ether, n-hexane, n-heptane or diethyl ether.

6. The process according to claim 4, wherein the anti-solvent is diisopropyl ether.

* * * * *